United States Patent
Tang et al.

(10) Patent No.: US 7,583,777 B2
(45) Date of Patent: Sep. 1, 2009

(54) METHOD AND APPARATUS FOR 3D RECONSTRUCTION OF IMAGES

(75) Inventors: Xiangyang Tang, Waukesha, WI (US); Jiang Hsieh, Brookfield, WI (US); Sandeep Dutta, Waukesha, WI (US); Roy Arnulf Helge Nilsen, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 308 days.

(21) Appl. No.: 10/895,704

(22) Filed: Jul. 21, 2004

(65) Prior Publication Data

US 2006/0018439 A1   Jan. 26, 2006

(51) Int. Cl.
    *A61B 6/00* (2006.01)
(52) U.S. Cl. ........................................................ 378/4
(58) Field of Classification Search ......... 378/204–210, 378/4, 901
    See application file for complete search history.

(56) References Cited

U.S. PATENT DOCUMENTS

| | | | | |
|---|---|---|---|---|
| 4,570,224 A | | 2/1986 | Shimoni et al. | 378/13 |
| 5,406,479 A | * | 4/1995 | Harman | 378/7 |
| 5,430,783 A | * | 7/1995 | Hu et al. | 378/15 |
| 5,881,123 A | * | 3/1999 | Tam | 378/4 |
| 5,887,047 A | | 3/1999 | Bailey et al. | 378/4 |
| 5,999,587 A | | 12/1999 | Ning et al. | 378/4 |
| 6,115,446 A | * | 9/2000 | Pan | 378/4 |
| 6,196,715 B1 | * | 3/2001 | Nambu et al. | 378/197 |
| 6,233,303 B1 | | 5/2001 | Tam | 378/4 |
| 6,240,157 B1 | * | 5/2001 | Danielsson | 378/15 |
| 6,263,040 B1 | | 7/2001 | Hsieh | 378/15 |
| 6,269,141 B1 | * | 7/2001 | Proksa et al. | 378/19 |
| 6,275,561 B1 | * | 8/2001 | Danielsson | 378/15 |
| 6,324,243 B1 | | 11/2001 | Edic et al. | 378/4 |
| 6,343,108 B1 | * | 1/2002 | Heuscher | 378/4 |
| 6,411,670 B1 | | 6/2002 | Besson | 378/4 |
| 6,415,012 B1 | * | 7/2002 | Taguchi et al. | 378/15 |

(Continued)

FOREIGN PATENT DOCUMENTS

EP        0919954 A1        6/1999

(Continued)

OTHER PUBLICATIONS

Longitudinal Aliasing in Multislice Helical Computed Tomography: Sampling and Cone-Beam Effects, La Riviere et al., IEEE Transactions on Medical Imgaing, vol. 21, No. 11, Nov. 2002.*

(Continued)

*Primary Examiner*—Edward J Glick
*Assistant Examiner*—Alexander H Taningco
(74) *Attorney, Agent, or Firm*—Armstrong Teasdale LLP

(57) ABSTRACT

A method for producing an image of an object includes scanning an object with an imaging apparatus to collect projection data of the object utilizing cone sampling. The projection data is rebinned in a row-wise, fan-to-parallel fashion to produce rebinned data and the rebinned data is view-weighted to produce view-weighted data. The method further includes filtering the view-weighted data utilizing a row-wise ramp filter to produce filtered data and generating an image of the object utilizing the filtered data and a three-dimensional (3D) backprojection.

45 Claims, 9 Drawing Sheets

U.S. PATENT DOCUMENTS

| | | | |
|---|---|---|---|
| 6,418,184 B1 * | 7/2002 | Wang et al. | 378/15 |
| 6,490,334 B1 * | 12/2002 | Wang et al. | 378/15 |
| 6,574,297 B2 * | 6/2003 | Tam | 378/15 |
| 6,574,298 B2 | 6/2003 | Heischer | 378/15 |
| 6,751,283 B2 | 6/2004 | Van de Haar | 378/17 |
| 6,778,629 B1 * | 8/2004 | Danielsson et al. | 378/15 |
| 6,839,400 B2 * | 1/2005 | Bruder et al. | 378/4 |
| 7,245,755 B1 * | 7/2007 | Pan et al. | 382/131 |
| 2003/0161443 A1 * | 8/2003 | Xiao et al. | 378/210 |
| 2003/0223533 A1 | 12/2003 | Hsieh et al. | 378/19 |
| 2004/0069951 A1 | 4/2004 | Jones et al. | 250/369 |
| 2004/0081279 A1 | 4/2004 | Brunnett | 378/98.8 |
| 2004/0114707 A1 * | 6/2004 | Bruder et al. | 378/4 |
| 2004/0136608 A1 * | 7/2004 | Rosenfeld | 382/276 |
| 2004/0252806 A1 * | 12/2004 | Taguchi et al. | 378/4 |
| 2005/0047542 A1 * | 3/2005 | Chen | 378/19 |
| 2005/0100124 A1 * | 5/2005 | Hsieh et al. | 378/4 |

FOREIGN PATENT DOCUMENTS

| | | | |
|---|---|---|---|
| EP | 0997849 A2 | 5/2000 | |
| EP | 1000408 B1 | 5/2000 | |
| EP | 0592093 B1 | 1/2001 | |
| EP | 0430549 B1 | 3/2002 | |
| WO | WO 01/80184 A1 | 10/2001 | |
| WO | WO 03/085390 A2 | 10/2003 | |

OTHER PUBLICATIONS

Schaller et al., A New Approximate Algorithm for Image Reconstruction in Cone-Beam Spiral CT at Small Cone-Angles, 1997, IEEE, pp. 1703-1709.*

Schaller et al., New, efficient Fourer-reconstruction method for approximate image reconstruction in spiral cone-beam CT at small cone angles, Medical Imaging 1997: Physics of Medical Imaging.*

Turbell, Cone-Beam Reconstruction Using Filtered Backprojection, Department of Electrical Engineering, Dissertation No. 672, Feb. 2001, pp. 1-74.*

Sourbelle, Performance Evaluation of Exact and Approximate Cone-Beam Algorithms in Spiral Computed Tomography, Berichte Aus Dem Institut Fur Medizinische Physic Der . . . Erlange-Nurnberg, Mar. 2002, pp. 1-3.*

Hsieh, Jiang; "Nonstationary Noise Characteristics of the Helical Scan and Its Impact on Image Quality and Artifcats"; *Med. Phys.*; pp. 1375-1384; vol. 24, No. 9; Sep. 1997.

Hsieh, Jiang; "A General Approach to the Reconstruction of X-ray Helical Computed Tomography"; *Med. Phys.*; pp. 221-229; vol. 23, No. 2; Feb. 1996.

Wang, GE; Lin, Tein-Hsiang; Cheng, Ping-Chin; Shinozaki, Douglas M.; "A General Coene-Beam Reconstruction Algorithm"; *IEEE Transaction and Medical Imaging*; pp. 489-496; vol. 12, No. 3; Sep. 1993.

Crawford, Carl R; King, Kevin F.; "Computed Tomography Scanning with Simultaneous Patent Translation"; *Med. Phys.*; pp. 967-982; vol. 17, No. 6; Nov./Dec. 1990.

Feldkamp, L.A.; Davis, L.C.; Kress, J.W.; "Practical Cone-Beam Algorithm"; *Journal of Optical Society of America*; pp. 612-619, col. 1, No. 6; Jun. 1984.

* cited by examiner

METHOD AND APPARATUS FOR 3D RECONSTRUCTION OF IMAGES

BACKGROUND OF THE INVENTION

This invention relates generally to the reconstruction of images and more particularly to methods and apparatus for 3D (three dimensional) reconstruction of images using virtual parallel sampling and/or view weighted backprojection.

With the development of three-dimensional (3D) or cone beam (CB) filtered backprojection (FBP) reconstruction algorithms, multi-detector-row CT scanners are evolving into volumetric CT (VCT) scanners. One of the most practical CB FBP reconstruction algorithm is the "FDK" algorithm proposed by Feldkamp, David and Kress in "Practical cone beam algorithm," J. Opt. Soc. Am. A, vol. 1, pp. 612-619, 1984. A helical FDK algorithm to handle helical CB data acquisition geometry is described in G. Wang, T. H. Lin, P. C. Cheng and D. M. Shinozaki, "A general cone-beam reconstruction algorithm," IEEE Trans. Med. Imag., vol. 12, pp. 486-496, 1993.

One common feature of both the original FDK and helical FDK algorithms is a $1/L^2$ factor in the 3D backprojection, in which L is the distance between the x-ray focal spot and the image pixel to be reconstructed. It is well recognized that the location-dependent $1/L^2$ factor results in computational complexity in the backprojection and non-uniform noise characteristics in tomographic images. To overcome these shortcomings, a modified FDK algorithm is described in U.S. Pat. No. 6,263,040 B1 (assigned to General Electric Company) by removing the $1/L^2$ from the 3D backprojection, in which a sequential triggering technique is employed to obtain cone-tilted parallel sampling (namely real 3D parallel sampling) from 3D cone sampling. However, this sequential triggering technique involves increased design and manufacturing complexities.

BRIEF DESCRIPTION OF THE INVENTION

Some configurations of the present invention therefore provide a method for producing an image of an object. The method includes scanning an object with an imaging apparatus to collect projection data of the object utilizing cone sampling. The projection data is rebinned in a row-wise, fan-to-parallel fashion to produce rebinned data and the rebinned data is view-weighted to produce view-weighted data. The method further includes filtering the view-weighted data utilizing a row-wise ramp filter to produce filtered data and generating an image of the object utilizing the filtered data and a three-dimensional (3D) backprojection.

In another aspect, some configurations of the present invention provide a method producing an image of an object that includes scanning an object with an imaging apparatus to collect projection data of the object utilizing cone sampling and rebinning the projection data in a row-wise, fan-to-parallel fashion to produce rebinned data. The method further includes filtering the rebinned data utilizing a row-wise ramp filter to produce filtered data, view-weighting the filtered data utilizing a 3D weighting function to produce view-weighted data, and generating an image of the object utilizing the view-weighted data and a 3D backprojection.

In yet another aspect, some configurations of the present invention provide an imaging apparatus that includes a radiation source and a multi-row detector array. The radiation source is configured to project a radiation beam through an object towards the detector array. The apparatus is configured to scan the object to collect projection data of the object utilizing cone sampling, and rebin the projection data in a row-wise, fan-to-parallel fashion to produce rebinned data. The apparatus is also configured to view-weight the rebinned data to produce view-weighted data, filter the view-weighted data utilizing a row-wise ramp filter to produce filtered data, and generate an image of the object utilizing the filtered data and a three-dimensional (3D) backprojection.

In still another aspect, some configurations of the present invention provide an imaging apparatus having a radiation source and a multi-row detector array. The radiation source is configured to project a radiation beam through an object towards the detector array. The apparatus is configured to scan an object to collect projection data of the object utilizing cone sampling and rebin the projection data in a row-wise, fan-to-parallel fashion to produce rebinned data. The apparatus is further configured to filter the rebinned data utilizing a row-wise ramp filter to produce filtered data, view-weight the filtered data utilizing a three-dimensional (3D) weighting function to produce view-weighted data, and generate an image of the object utilizing the view-weighted data and a (3D) backprojection.

Configurations of the present invention that provide virtual 3D parallel sampling realize this sampling using row-wise fan-to-parallel rebinning. By incorporating a view weighting function, various configurations of the present invention are applicable in both partial and over-scanning cases in both axial and helical x-ray source trajectories, thereby facilitating development of VCT applications, although configurations of the present invention are not limited x-ray source or VCT applications. Moreover, reduced design and manufacturing complexities result in cost savings.

DETAILED DESCRIPTION OF THE INVENTION

Figure 1:
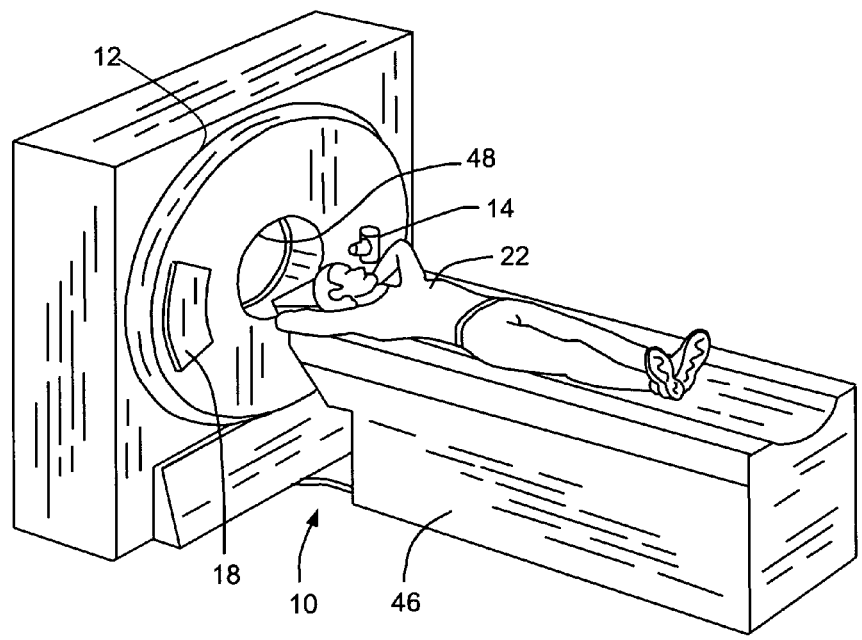
FIG. 1 is a perspective view of a configuration of a computed tomographic imaging apparatus.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image. Thus, methods and apparatus are described herein that have a technical effect of producing a three-dimensional (3D) image of a scanned object.

Figure 2:
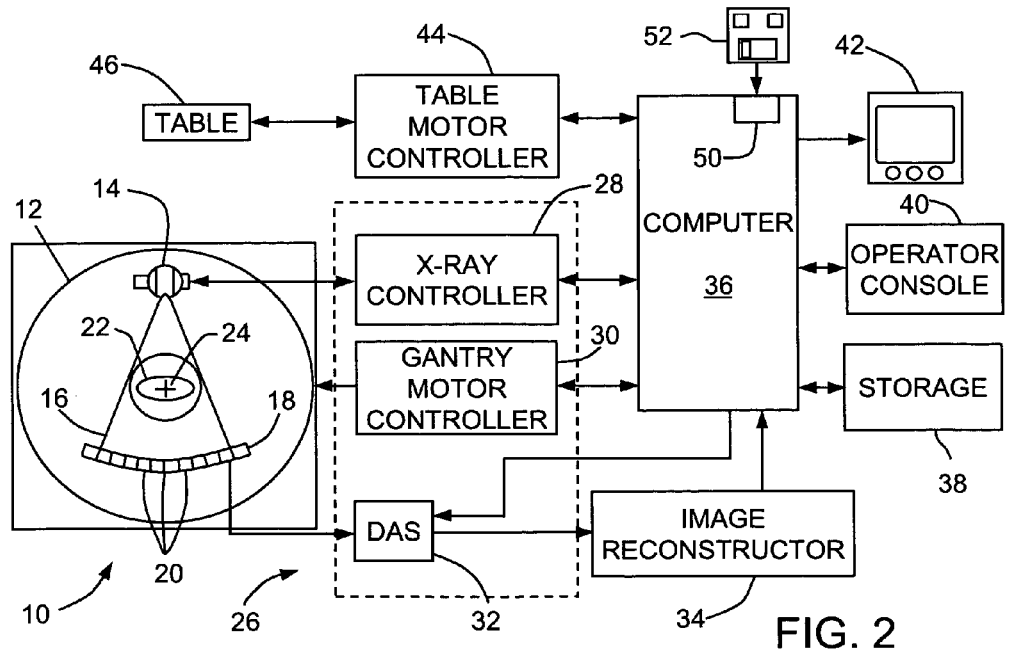
FIG. 2 is a functional block diagram of the computed tomographic imaging apparatus illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has a radiation source such as an x-ray tube 14 (also called x-ray source 14 herein) that projects a beam of radiation such as x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging radiation (e.g., x-ray) beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 or other suitable display device allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). In some configurations, computer 36 and/or image reconstructor 34 is/are programmed to perform functions described herein. Also, as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
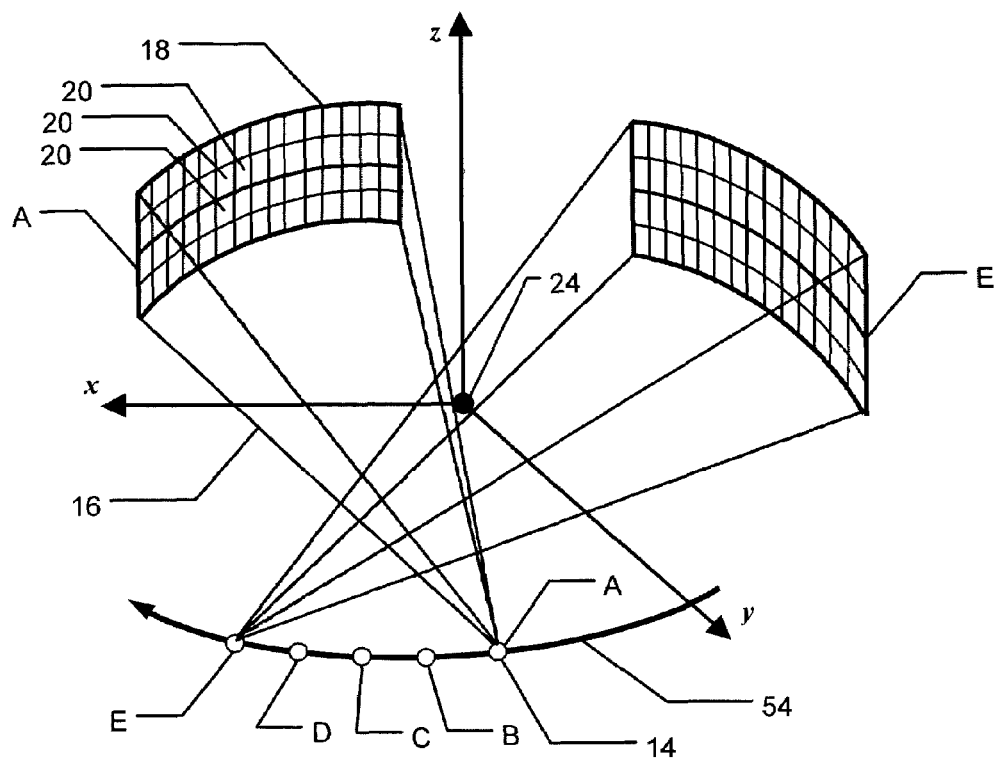
FIG. 3 is a perspective representation of the geometry of an x-ray source trajectory and cone sampling pattern in an associated x-ray detector, wherein the detector is either a curved array, such as the cylindrical detector array depicted in FIG. 3, or a flat panel array.

In some configurations, x-ray detector array 18 is either a flat panel or curved array and x-ray source 14 follows a trajectory 54, a portion of which is illustrated in FIG. 3. Trajectory 54 is either a circle or helix. In following trajectory 54, x-ray source 14 passes successively through positions A, B, C, D, and E. X-ray source 14 emits an x-ray beam 16 that impinges upon x-ray detector array 18. Two exemplary positions A and E of x-ray detector array 18 are shown. In a rotating gantry CT imaging system such as system 10, x-ray detector array 18 also follows a trajectory that corresponds to x-ray source 14, although the trajectory is not explicitly indicated in FIG. 3; hence, positions A and E of x-ray detector array 18 correspond, respectively, to positions A and E of x-ray source 14. Between positions A and E of x-ray source 14 on trajectory 54, several intermediate positions B, C, and D of x-ray source 14 are also indicated, although corresponding x-ray beam 16 orientations and x-ray detector array 18 positions are omitted for clarity of illustration. (Positions A, B, C, D, and E represent discrete positions in a trajectory. The discrete positions are indicative of certain positions of a single x-ray source and a single x-ray detector array, and are not intended to suggest that the single x-ray source and/or single x-ray detector array are operative only at discrete locations along their trajectories.)

Figure 4:
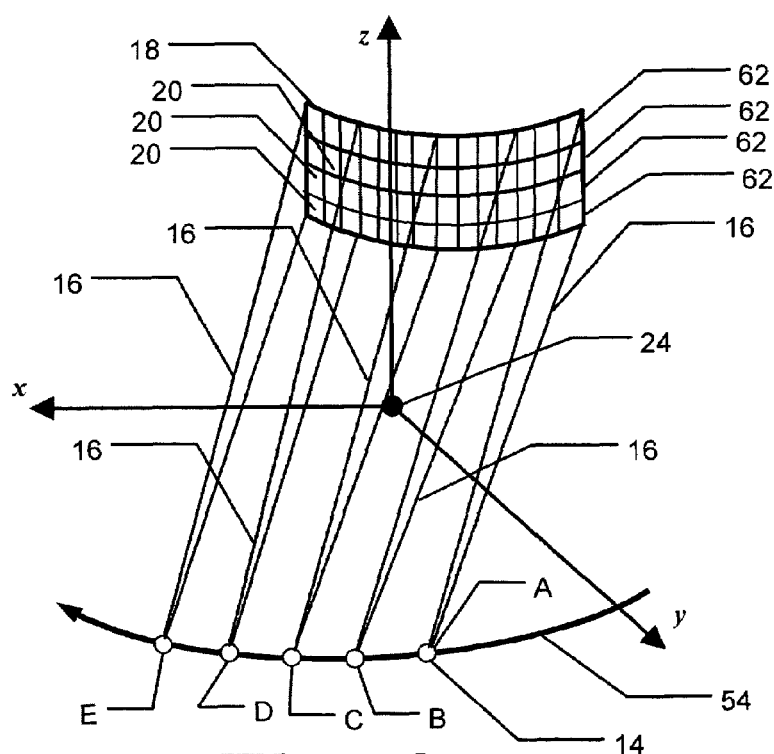
FIG. 4 is a representation of virtual 3D parallel sampling rebinned via row-wise fan-to-parallel interpolations from a series of cone sampling, such as from the cone sampling pattern represented by FIG. 3.

In some configurations, FIG. 4 is representative of the geometry of a virtual 3D parallel sampling rebinned from a series of cone sampling illustrated in FIG. 3, obtained via row-wise fan to parallel interpolation. Such configurations utilize any of several row-wise fan-to-parallel interpolation methods to carry out the fan-to-parallel rebinning process. Also, any of several known techniques can be utilized for fan-to-parallel rebinning to trade off between image quality (for example, spatial resolution and spatial resolution uniformity) and image generation speed. Suitable techniques include but are not limited to:

(a) Up-sampling or under-sampling in virtual parallel sampling, i.e., the view number per rotation of virtual parallel sampling can be larger or smaller than that of cone sampling. This technique is referred to herein as interview up-sampling or under-sampling.

(b) Interview up-sampling or under-sampling that need not be uniform over the virtual source trajectory, and which can be adaptively adjusted according to the spatial frequency variation of the object to be reconstructed as a function over view angle. This technique is referred to herein as adaptive interview up-sampling or under-sampling.

(c) Up-sampling or under-sampling within each virtual parallel view rebinned from cone views. This technique is referred to herein as intraview up-sampling or under-sampling.

(d) Intraview up-sampling or under-sampling that need not be uniform over the whole virtual parallel view, and which can be adaptively adjusted according to the spatial frequency variation of the object to be reconstructed as a function over virtual detector cells. This technique is referred to herein as adaptive intraview up-sampling and under-sampling.

(e) Intraview up-sampling or under-sampling that depends upon view angle relative to the reconstruction plane (i.e., the intraview up-sampling or under-sampling varies over view angle) is referred to herein as view-angle or location dependent intraview up-sampling or under-sampling.

Figure 5:
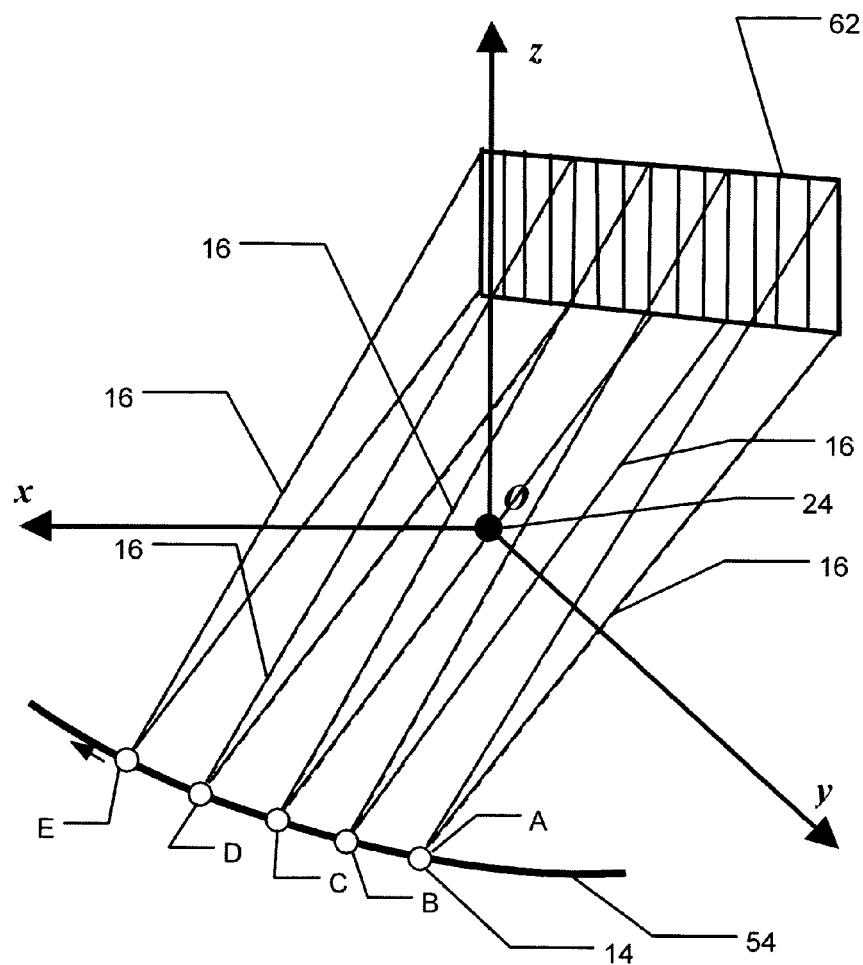
FIG. 5 is a representation of the geometry of a virtual 3D parallel resampling of a virtual flat x-ray detector resulting from rebinning projection data in the virtual convex x-ray detector shown in FIG. 4.

In some configurations and referring to FIGS. 4 and 5, virtual convex x-ray detector 18 is transformed into a virtual flat x-ray detector 62 by appropriately rebinning projection data. A representation of the transformed geometry is shown in FIG. 5. Due to the geometrical transformation or data rebinning, detector rows (not shown in FIG. 5) in virtual flat x-ray detector 62 may no longer be parallel even though their counterpart detector rows 64 in virtual convex x-ray detector 18 are parallel to one another.

(f) Any of techniques (a) through (e), given a non-uniform grid on which a tomographic image is to be reconstructed and adjusted accordingly.

Let $f(x,y,z)$ represent the object to be reconstructed. In some configurations of the present invention, a reconstruction using virtual 3D parallel sampling is written:

$$f(x, y, z) = \frac{\pi}{(\beta_{max} - \beta_{min})} \int_{\beta_{min}}^{\beta_{max}} \left[ d^2 / (d^2 + Z^2(z))^{1/2} \right] \quad (1)$$
$$\left[ \int_{-\infty}^{+\infty} w(\alpha, \beta, t(x, y)) S_\beta(\omega, Z(z)) e^{j2\pi\omega x} |\omega| d\omega \right] d\beta$$

and $$S_\beta(\omega, Z(z)) = \int_{-\infty}^{\infty} P_\beta(t(x, y)Z(z)) e^{-j2\pi\omega t} dt \quad (2)$$

wherein $P_\beta(t(x,y),Z(z))$ is the projection of the pixel to be reconstructed on the virtual detector under virtual 3D parallel sampling;

$t(x,y)$ is the orthogonal distance between $(x,y,z)$, the pixel to be reconstructed, and the z axis;

$w(\alpha,\beta,t(x,y))$ is the 3D view weighting function;

d is the orthogonal distance between the x-ray focal spot and the virtual detector; and $Z(z)$ is the height of the projection of the pixel $(x,y,z)$ in the virtual detector under virtual 3D parallel sampling.

α represents the cone angle of the x-ray passing through pixel $(x,y,z)$; and β represents the view angle associated with $(x,y,z)$;

$\beta_{min}$ is the start view angle in radians; and $\beta_{max}$ is the end view angle in radians.

In principle, the view weighting function $w(\alpha,\beta,t(x,y))$ in eq. (1) can be dependent on cone angle α and view angle β only, i.e., $w(\alpha,\beta,t(x,y))=w(\alpha,\beta,\circ)\equiv w(\alpha,\beta)$. Consequently, eq. (1) can be rearranged as $$f(x, y, z) = \frac{\pi}{(\beta_{max} - \beta_{min})} \int_{\beta_{min}}^{\beta_{max}} w(\alpha, \beta) \left[ d^2 / (d^2 + Z^2(z))^{1/2} \right] \quad (3)$$
$$\left[ \int_{-\infty}^{+\infty} S_\beta(\omega, Z(z)) e^{j2\pi\omega x} |\omega| d\omega \right] d\beta$$

Thus, in various configurations of the present invention, view weighting is applied after filtering. However, eq. (1) still provides flexibility in dealing with imperfect x-ray detectors under practical situations, as well as the potentiality of obtaining the most achievable temporal resolution in functional CT imaging.

The inner integration over variable ω in eqs. (1) and (3) represents a row-wise 1D ramp filtering as used in known methods of CT reconstruction. The row-wise 1D ramp filtering is spatially parallel to the x-y plane when eqs. (1)-(3) are applied under a circular x-ray source trajectory, but is tangential to the source trajectory under a helical scan mode. Also, the linear grid on which the row-wise 1D filtering is accomplished is adjusted accordingly when techniques (c) through (e) are utilized.

Figure 6:
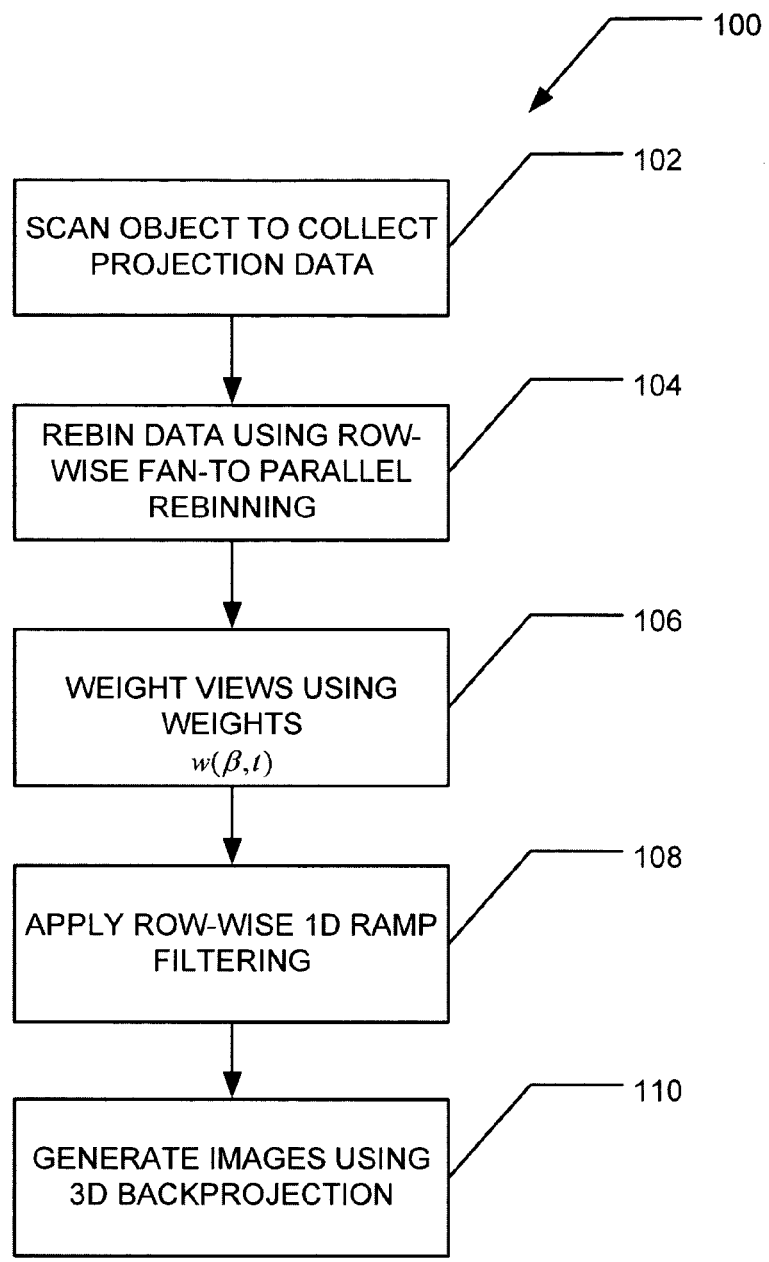
FIG. 6 is a flow chart representing some configurations of the reconstruction in which row-wise one-dimensional (1D) ramp filtering is performed after view weighting.

Thus, in some configurations and referring to flow chart 100 of FIG. 6, a technical effect of the present invention is achieved by a user operating CT imaging apparatus 10 to scan an object 22 at 102 to collect projection data. The scanning can be performed, for example, by operating CT imaging apparatus 10 to scan an object 22 as described above. The projection data obtained from the scanning is then subjected to a row-wise fan-to-parallel beam rebinning at 104. The rebinned data is then view-weighted using weights $w(\alpha,\beta,t(x,y))$ at 106, and the view-weighted data is then subjected to a row-wise 1D ramp filtering at 108 followed by a 3D backprojection at 110 to produce an image of object 22. Configurations represented by the flow chart of FIG. 6 reflect the transformations described by eq. (1) above.

Figure 7:
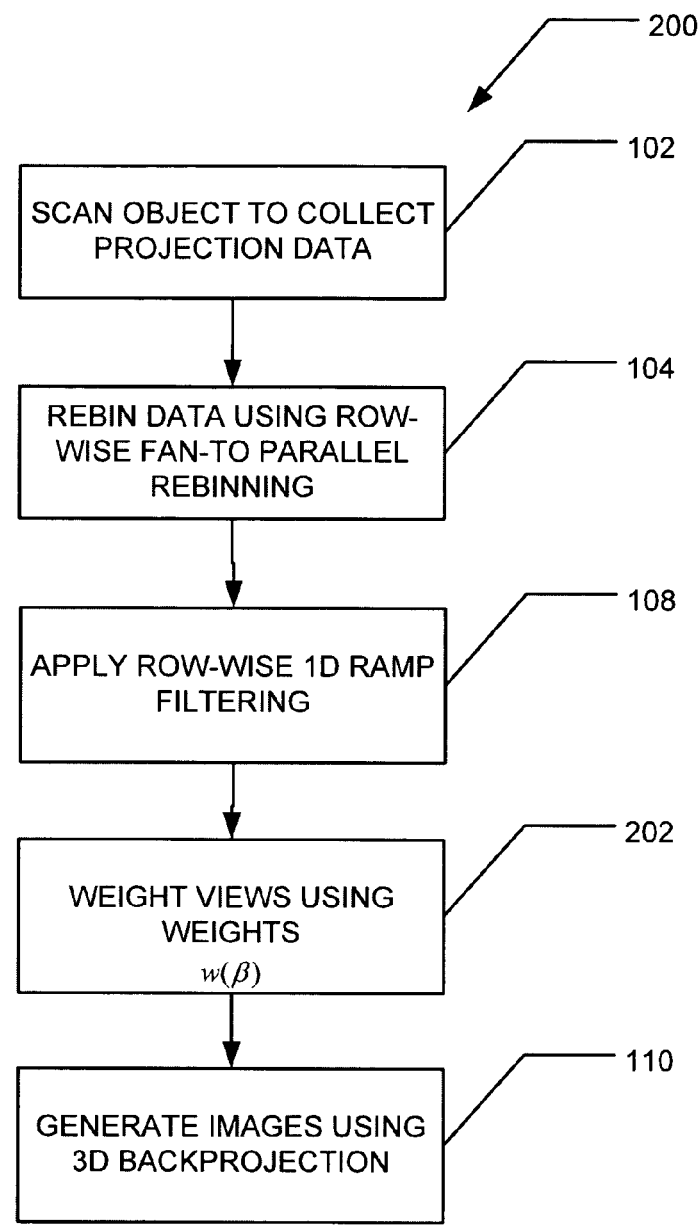
FIG. 7 is a flow chart representing some configurations of the present invention in which row-wise 1D ramp filtering is performed before view weighting.

In some configuration and referring to flow chart 200 of FIG. 7, after operating CT apparatus 10 to scan an object 22 at 102 to collect projection data and row-wise fan-to-parallel rebinning is performed at 104, the rebinned data is subjected first to row-wise ramp filtering 108 and then the filtered data is subjected to view weighting at 200 using weights $w(\alpha,\beta)$. The weighted data is then used in a 3D backprojection at 110 to produce an image of object 22. The view weighting at 200 is implemented after the row-wise 1D ramp filtering at 108 because the view weighting function $w(\alpha,\beta)$ is not dependent on $t(x,y)$. This independence of $t(x,y)$ (rather than the dependence on $t(x,y)$ of weights $w(\alpha,\beta,t(x,y))$ at 106 of flow chart 100 of FIG. 6) results in significantly improved computational efficiency because all projection data under virtual 3D parallel sampling need be filtered only once. Examples of suitable view weighting methods include, but are not limited to, those described by C. R. Crawford and K. F. King in "Computed tomography scanning with simultaneous patient translation," Med. Phys. 17(6), pp 967-982, 1990 and by J. Hsieh in "A general approach to the reconstruction of x-ray helical computed tomography," Med. Phys. Vol. 23 (2), pp 221-229, 1996. A significant feature of configurations of the present invention that utilize 3D reconstruction methods using virtual 3D parallel sampling is that the 1D ramp filtering is adaptively implemented along the tangential direction of an x-ray source trajectory.

Exemplary configurations of the present invention described herein utilize a CT imaging apparatus and x-ray radiation. However, configurations of the present invention are not limited to CT imaging apparatus and x-ray radiation. For example, some configurations of the present invention employ other types of radiation, even, for example, ultrasound radiation.

Figure 8:
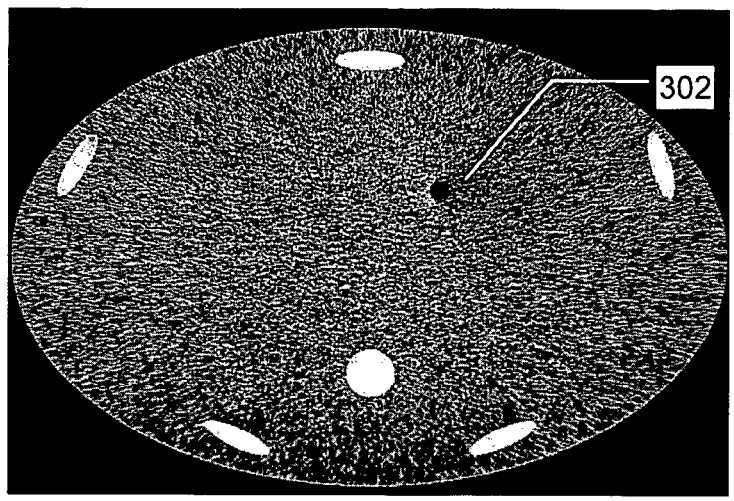
FIG. 8 is a reconstructed image of an HBP phantom utilizing a prior art FDK reconstruction algorithm with horizontal 1D ramp filtering.
Figure 9:
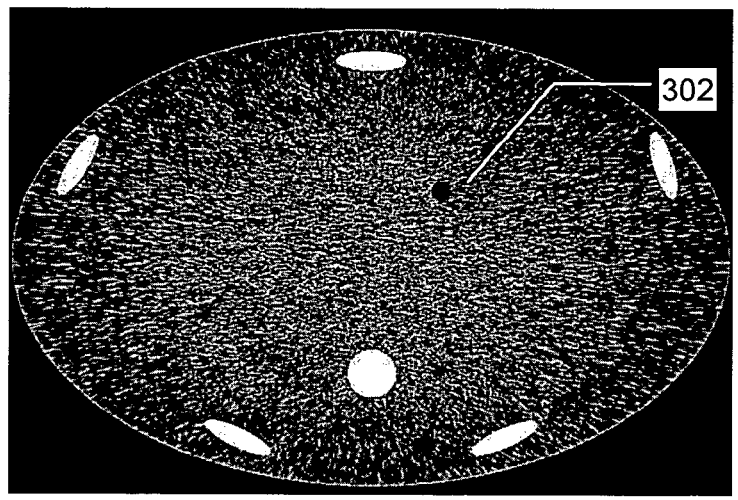
FIG. 9 is a reconstructed image of the same HBP phantom as FIG. 8 utilizing a configuration of a 3D reconstruction method utilizing virtual parallel sampling in which tangential 1D ramp filtering is inherently implemented. In both FIG. 7 and FIG. 8, W/L=100/0, the detector is 64×0.625 mm, the radius of the detector is 541.0 mm, and the pitch is 63/64.

FIG. 8 and FIG. 9 provide a comparison of shading/glaring artifact suppression in axial views of an HBP phantom. FIG. 8 is a reconstruction using a prior art helical FDK algorithm with horizontal 1D ramp filtering and shows, among other things, shading in region 302. FIG. 9 is a reconstruction of the same HBP phantom as FIG. 8 utilizing a configuration of a 3D reconstruction method utilizing virtual 3D parallel sampling in which tangential 1D ramp filtering is inherently implemented. FIG. 9 shows, among other things, a substantial reduction in the shading artifact in region 302.

Figure 10:
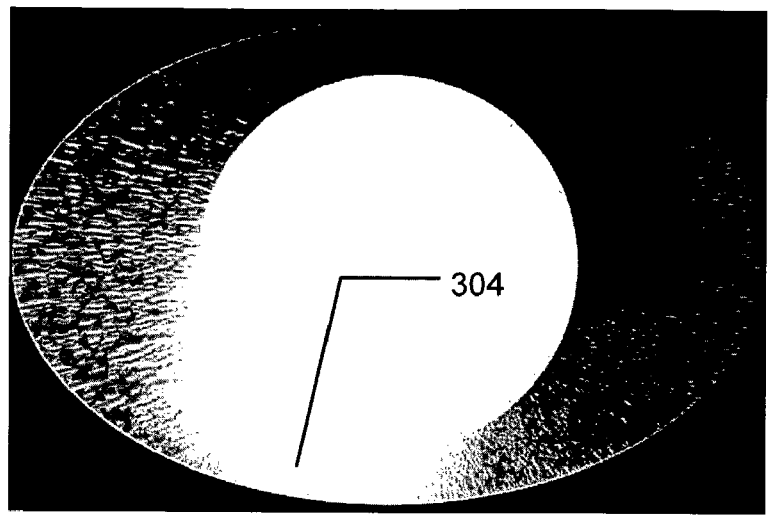
FIG. 10 is a reconstructed image of a Defrise phantom in an axial view reconstructed using a prior art helical FDK algorithm with horizontal 1D ramp filtering.
Figure 11:
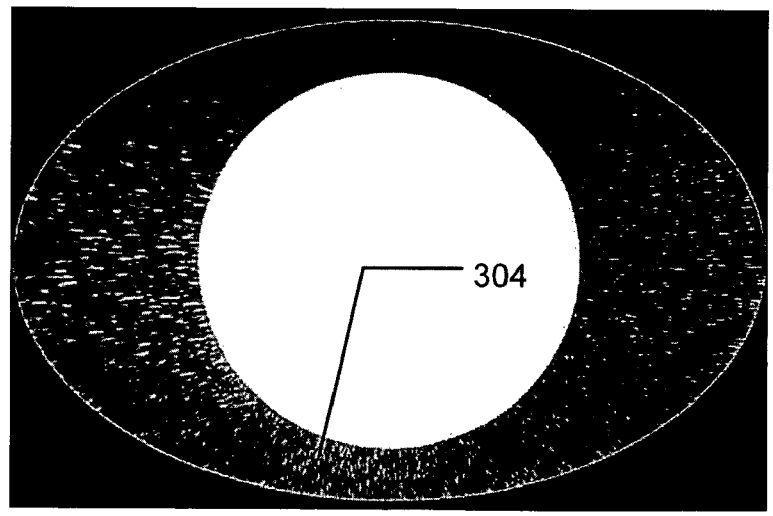
FIG. 11 is a reconstructed image of the same Defrise phantom as FIG. 10 in an axial view reconstructed using a configuration of a 3D reconstruction method utilizing virtual parallel sampling in which tangential 1D ramp filtering is inherently implemented. In both FIG. 10 and FIG. 11, W/L=300/0, the detector is 64×0625 mm, the radius of the detector is 541.0 mm, and the pitch is 63/64.

FIG. 10 and FIG. 11 provide a comparison of shading/glaring artifact suppression in axial views of a Defrise phantom. FIG. 10 is a reconstructed image using a prior art helical FDK algorithm with horizontal 1D ramp filtering. Considerable glare is noted at region 304. FIG. 11 is a reconstructed image of the same phantom as FIG. 10. However, FIG. 11 is reconstructed using a configuration of a 3D reconstruction method utilizing virtual 3D parallel sampling in which tangential 1D ramp filtering is inherently implemented. The glare at region 304 is greatly reduced in FIG. 11.

Figure 12:
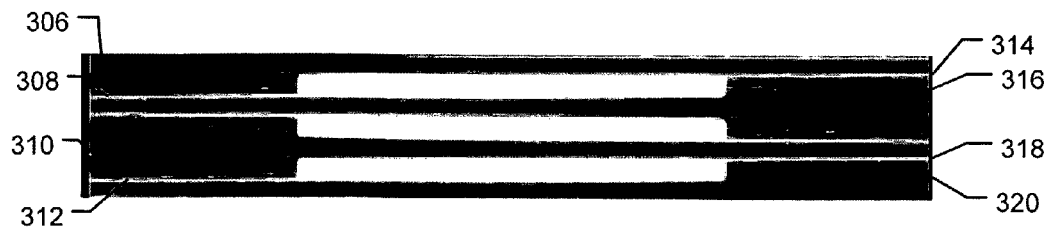
FIG. 12 is a reconstructed image of a Defrise phantom in a coronal reformatted view reconstructed using a prior art helical FDK algorithm with horizontal 1D ramp filtering.
Figure 13:
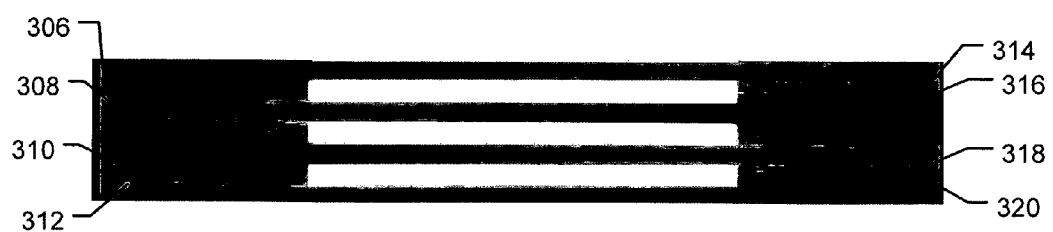
FIG. 13 is a reconstructed image of the same Defrise phantom as FIG. 12 in a coronal reformatted view reconstructed using a configuration of a 3D reconstruction method utilizing virtual parallel sampling in which tangential 1D ramp filtering is inherently implemented. In both FIG. 12 and FIG. 13, W/L=300/0, the detector is 64×0.625 mm, the radius of the detector is 541.0 mm, and the pitch is 63/64.

FIG. 12 and FIG. 13 provide a comparison of shading/glaring artifact suppression and geometric distortion in coronal reformatted views of a Defrise phantom. FIG. 12 is a reconstructed image using a prior art helical FDK algorithm with horizontal 1D ramp filtering. The reconstructed image of FIG. 12 shows considerable glare and shading at numerous locations, including locations 306, 308, 310, 312, 314, 316, 318, and 320. FIG. 13 is a reconstructed image of the same phantom as FIG. 12. However, FIG. 13 is reconstructed using a configuration of a 3D reconstruction method utilizing virtual parallel sampling in which tangential 1D ramp filtering is inherently implemented. A significant reduction in glare and shading artifacts is noted, including but not limited to the artifacts at locations 306, 308, 310, 312, 314, 316, 318, and 320. Geometric distortion is also reduced.

Figure 14:
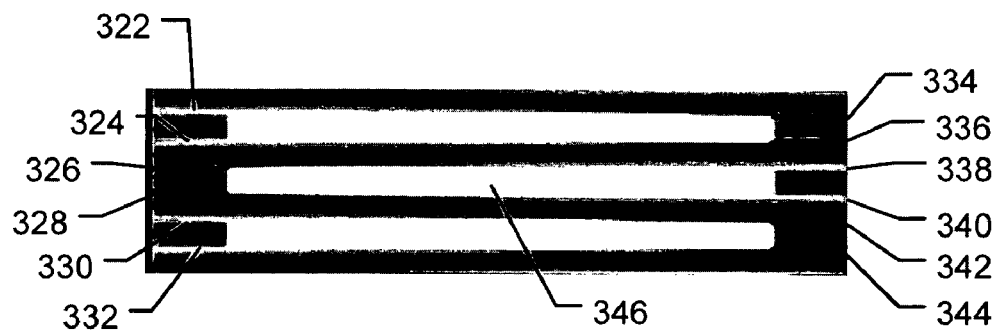
FIG. 14 is a reconstructed image of a Defrise phantom in a sagittal reformatted view reconstructed using a prior art helical FDK algorithm with horizontal 1D ramp filtering.
Figure 15:
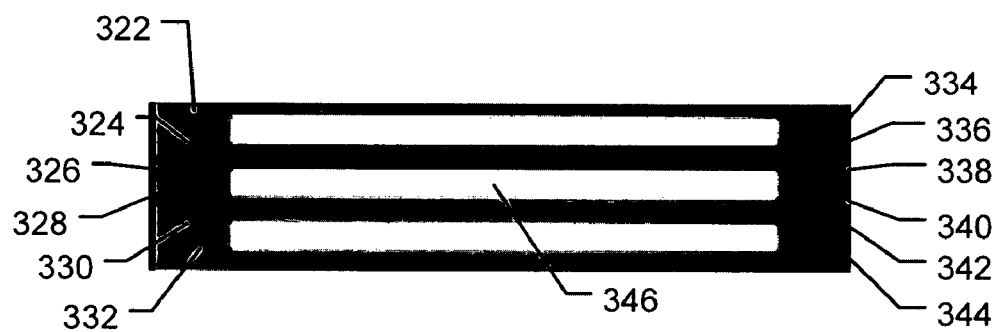
FIG. 15 is a reconstructed image of the same Defrise phantom as FIG. 14 in a sagittal reformatted view reconstructed using a configuration of a 3D reconstruction method utilizing virtual parallel sampling in which tangential 1D ramp filtering is inherently implemented. In both FIG. 14 and FIG. 15, W/L=300/0, the detector is 64×0.625 mm, the radius of the detector is 541.0 mm, and the pitch is 63/64.

FIG. 14 and FIG. 15 provide a comparison of shading/glaring artifact suppression and geometric distortion in sagittal reformatted views of a Defrise phantom. FIG. 14 is a reconstructed image using a prior art helical FDK algorithm with horizontal 1D ramp filtering. The reconstructed image of FIG. 15 shows considerable glare and shading at numerous locations, including locations 322, 324, 326, 328, 330, 332, 334, 336, 338, 340, 342, and 344. In addition, considerable geometric distortion is evident in various shapes, including but not limited to shape 346. FIG. 15 is a reconstructed image of the same phantom as FIG. 12. However, FIG. 13 is reconstructed using a configuration of a 3D reconstruction method utilizing virtual parallel sampling in which tangential 1D ramp filtering is inherently implemented. A significant reduction in glare and shading artifacts is noted, including but not limited to the artifacts at locations 322, 324, 326, 328, 330, 332, 334, 336, 338, 340, 342, and 344. Additionally, geometric distortion is reduced, including but not limited to shape 346.

It will thus be observed that configurations of the present invention significantly improve the suppression of shading and glaring artifacts resulting from inconsistencies in cone beam helical data acquisition in volumetric CT scanning systems as well as the speed of image generation. In addition, configurations of the present invention improve suppression of distortion resulting from inconsistencies in cone beam helical data acquisition in volumetric CT scanning systems. Furthermore, configurations of the present invention have improved noise characteristics and can provide better dose efficiency than other known scanning algorithms implementations including various exact CT reconstruction algorithm implementations.

In addition, row-wise fan-to-parallel rebinning to generate virtual 3D parallel sampling avoids design and manufacturing complexities of some known systems employing sequential triggering. The incorporation of a view weighting function in the reconstruction process enables various configurations of the present invention to handle partial scan (i.e., view angle range smaller than 360 degrees) and over scan (i.e., view angle range larger than 360 degrees) under both circular and helical x-ray source trajectories. Various configurations of the present invention also provide flexibility by implementing view weighting either before filtering or after filtering, or even in the process of 3D backprojection.

While the invention has been described in terms of various specific embodiments, those skilled in the art will recognize that the invention can be practiced with modification within the spirit and scope of the claims.

What is claimed is:

1. A method for producing an image of an object, said method comprising:
    scanning the object with an imaging apparatus to collect projection data of the object utilizing cone sampling;
    performing virtual three-dimensional (3D) parallel sampling of the projection data by:
        rebinning the projection data in a row-wise, fan-to-parallel fashion to produce rebinned data;
        generating a virtual detector array based on the rebinned data;
        view-weighting the rebinned data of the virtual detector array to produce 3D view-weighted data; and
        filtering the 3D view-weighted data utilizing a tangential row-wise ramp filter to produce filtered data by implementing said filtering along rows of the virtual detector array and along a tangential direction with respect to a trajectory of a radiation source; and
    generating an image of the object utilizing the filtered data and a 3D backprojection.

2. A method in accordance with claim 1 wherein said rebinning the projection data comprises one of up-sampling and under-sampling the projection data in said virtual 3D parallel sampling, wherein a view number per rotation of said virtual 3D parallel sampling is one of larger and smaller than that of said cone sampling.

3. A method in accordance with claim 1 wherein said rebinning the projection data comprises one of up-sampling and undersampling that is non-uniform over a virtual source trajectory.

4. A method in accordance with claim 3 wherein said one of up-sampling and under-sampling is adaptively adjusted in accordance with a spatial frequency variation of the object as a function of view angle.

5. A method in accordance with claim 1 wherein said rebinning the projection data comprises one of up-sampling and under-sampling within virtual parallel views rebinned from cone views.

6. A method in accordance with claim 1 wherein said rebinning the projection data comprises one of intraview up-sampling and intraview under-sampling that is non-uniform over a virtual parallel view.

7. A method in accordance with claim 6 wherein said one of non-uniform intraview up-sampling and non-uniform intraview under-sampling is adaptively adjusted according to a spatial frequency variation of the object as a function over virtual detector cells.

8. A method in accordance with claim 6 wherein said one of non-uniform intraview up-sampling and non-uniform intraview under-sampling is adaptively adjusted according to a spatial frequency variation of the object as a function over virtual detector cells.

9. A method in accordance with claim 6 wherein said rebinning the projection data comprises one of view-angle dependent intraview up-sampling and view-angle dependent intraview under-sampling.

10. A method in accordance with claim 1 wherein said rebinning the projection data is performed on a non-uniform grid on which a tomographic image of the object is to be reconstructed.

11. A method in accordance with claim 1 wherein the row-wise filter is a one-dimensional ramp filter.

12. A method in accordance with claim 1 wherein said view-weighting the rebinned data further comprises view-weighting the rebinned data using at least a distance between an x-ray focal spot and the virtual detector array.

13. A method in accordance with claim 1 wherein generating an image of the object utilizing the filtered data and a 3D backprojection further comprises performing the 3D view weighting in the 3D backprojection.

14. A method for producing an image of an object, said method comprising:
    scanning the object with an imaging apparatus to collect projection data of the object utilizing cone sampling;
    performing virtual three-dimensional (3D) parallel sampling of the projection data by:
        rebinning the projection data in a row-wise, fan-to-parallel fashion to produce rebinned data;
        generating a virtual detector array based on the rebinned data;

filtering the rebinned data of the virtual detector array utilizing a tangential row-wise ramp filter to produce filtered data by implementing said filtering along rows of the virtual detector array and along a tangential direction with respect to a trajectory of a radiation source; and view-weighting the filtered data utilizing a 3D weighting function to produce 3D view-weighted data; and generating an image of the object utilizing the 3D view-weighted data and a 3D backprojection.

15. A method in accordance with claim 14 wherein the imaging apparatus is a CT imaging apparatus comprising an x-ray source and a x-ray detector on a rotating gantry.

16. A method in accordance with claim 14 wherein said rebinning the projection data comprises one of up-sampling and under-sampling the projection data in said virtual 3D parallel sampling, wherein a view number per rotation of said virtual 3D parallel sampling is one of larger and smaller than that of said cone sampling.

17. A method in accordance with claim 14 wherein said rebinning the projection data comprises one of up-sampling and undersampling that is non-uniform over a virtual source trajectory.

18. A method in accordance with claim 14 wherein said rebinning the projection data comprises one of up-sampling and under-sampling within virtual parallel views rebinned from cone views.

19. A method in accordance with claim 14 wherein said rebinning the projection data comprises one of intraview up-sampling and intraview under-sampling that is non-uniform over a virtual parallel view.

20. A method in accordance with claim 19 wherein said one of non-uniform intraview up-sampling and non-uniform intraview under-sampling is adaptively adjusted according to a spatial frequency variation of the object as a function over virtual detector cells.

21. A method in accordance with claim 14 wherein said rebinning the projection data is performed on a non-uniform grid on which a tomographic image of the object is to be reconstructed.

22. A method in accordance with claim 14 wherein the row-wise filter is a one-dimensional ramp filter.

23. An imaging apparatus comprising a radiation source and a multi-row detector array, said radiation source configured to project a radiation beam through an object towards said detector array, said apparatus configured to:

scan the object to collect projection data of the object utilizing cone sampling;

perform virtual three-dimensional (3D) parallel sampling of the projection data by:

rebinning the projection data in a row-wise, fan-to-parallel fashion to produce rebinned data;

generating a virtual detector array based on the rebinned data;

view-weighting the rebinned data of the virtual detector array to produce 3D view-weighted data; and filtering the 3D view-weighted data utilizing a tangential row-wise ramp filter to produce filtered data by implementing filtering along rows of the virtual detector array and along a tangential direction with respect to a trajectory of a radiation source; and generate an image of the object utilizing the filtered view-weighted data and a 3D backprojection.

24. An apparatus in accordance with claim 23 wherein the radiation source is an x-ray source and the detector array is an x-ray detector, and said radiation source and detector array are on a rotating gantry.

25. An apparatus in accordance with claim 23 wherein to rebin the projection data, said apparatus is configured to one of up-sample and under-sample the projection data in said virtual 3D parallel sampling, wherein a view number per rotation of said virtual 3D parallel sampling is one of larger and smaller than that of said cone sampling.

26. An apparatus in accordance with claim 23 wherein to rebin the projection data, said apparatus is configured to one of up-sample and undersample non-uniformly over a virtual source trajectory.

27. An apparatus in accordance with claim 26 configured to adaptively adjust the one of up-sampling and under-sampling in accordance with a spatial frequency variation of the object as a function of view angle.

28. An apparatus in accordance with claim 23 wherein to rebin the projection data, said apparatus is configured to one of up-sample and under-sample within virtual parallel views rebinned from cone views.

29. An apparatus in accordance with claim 23 to rebin the projection data, said apparatus is configured to one of intraview up-sample and intraview under-sample non-uniformly over a virtual parallel view.

30. An apparatus in accordance with claim 29 wherein said apparatus is configured to adaptively adjust said one of non-uniform intraview up-sampling and non-uniform intraview under-sampling according to a spatial frequency variation of the object as a function over virtual detector cells.

31. An apparatus in accordance with claim 29 configured to adaptively adjust said one of non-uniform intraview up-sampling and non-uniform intraview under-sampling according to a spatial frequency variation of the object as a function over virtual detector cells.

32. An apparatus in accordance with claim 23 wherein to rebin the projection data, said apparatus is configured to perform one of view-angle dependent intraview up-sampling and view-angle dependent intraview under-sampling.

33. An apparatus in accordance with claim 23 configured to perform said rebinning of the projection data on a non-uniform grid on which a tomographic image of the object is to be reconstructed.

34. An apparatus in accordance with claim 23 wherein the row-wise filter is a one-dimensional ramp filter.

35. An imaging apparatus comprising a radiation source and a multi-row detector array, said radiation source configured to project a radiation beam through an object towards said detector array, said apparatus configured to:

scan the object to collect projection data of the object utilizing cone sampling;

perform virtual three-dimensional (3D) parallel sampling of the projection data by:

rebinning the projection data in a row-wise, fan-to-parallel fashion to produce rebinned data;

generating a virtual detector array based on the rebinned data;

filtering the rebinned data of the virtual detector array utilizing a tangential row-wise ramp filter to produce filtered data by implementing filtering along rows of the virtual detector array and along a tangential direction with respect to a trajectory of a radiation source; and view-weighting the filtered data utilizing a 3D weighting function to produce 3D view-weighted data; and generate an image of the object utilizing the 3D view-weighted data and a 3D backprojection.

36. An apparatus in accordance with claim 35 wherein the radiation source is an x-ray source and the detector array is an x-ray detector, and said radiation source and detector array are on a rotating gantry.

37. An apparatus in accordance with claim 35 wherein to rebin the projection data, said apparatus is configured to one of up-sample and under-sample the projection data in said virtual 3D parallel sampling, wherein a view number per rotation of said virtual 3D parallel sampling is one of larger and smaller than that of said cone sampling.

38. An apparatus in accordance with claim 35 wherein to rebin the projection data, said apparatus is configured to one of up-sample and undersample non-uniformly over a virtual source trajectory.

39. An apparatus in accordance with claim 38 configured to adaptively adjust the one of up-sampling and under-sampling in accordance with a spatial frequency variation of the object as a function of view angle.

40. An apparatus in accordance with claim 35 wherein to rebin the projection data, said apparatus is configured to one of up-sample and under-sample within virtual parallel views rebinned from cone views.

41. An apparatus in accordance with claim 35 to rebin the projection data, said apparatus is configured to one of intra-view up-sample and intraview under-sample non-uniformly over a virtual parallel view.

42. An apparatus in accordance with claim 41 configured to adaptively adjust said one of non-uniform intraview up-sampling and non-uniform intraview under-sampling according to a spatial frequency variation of the object as a function over virtual detector cells.

43. An apparatus in accordance with claim 35 configured to perform said rebinning of the projection data on a non-uniform grid on which a tomographic image of the object is to be reconstructed.

44. An apparatus in accordance with claim 35 wherein the row-wise filter is a one-dimensional ramp filter.

45. An imaging apparatus in accordance with claim 35 wherein said apparatus is further configured to view-weight the rebinned data using a view weighting function that is not dependent on a distance between a pixel to be reconstructed and a Z-axis of said imaging apparatus, said Z-axis substantially perpendicular to said radiation beam.

* * * * *